US006787358B2

(12) United States Patent
Nelles et al.

(10) Patent No.: US 6,787,358 B2
(45) Date of Patent: Sep. 7, 2004

(54) METHOD OF FORMING A CELL PATTERN ON A SURFACE

(75) Inventors: Gabriele Nelles, Stuttgart (DE); Akio Yasuda, Stuttgart (DE); Wolfgang Knoll, Mainz (DE); Andreas Offenhäusser, Mainz (DE); Chi-Kong Yeung, Frampton (GB); Lars Lauer, Mainz (DE)

(73) Assignees: Sony International (Europe) GmbH, Berlin (DE); Max-Planck-Gesellschaft Zur Forderung der Wissenschaften E.V., Munich (DE)

( * ) Notice: Subject to any disclaimer, the term of this patent is extended or adjusted under 35 U.S.C. 154(b) by 323 days.

(21) Appl. No.: 10/033,150

(22) Filed: Oct. 19, 2001

(65) Prior Publication Data

US 2002/0095219 A1 Jul. 18, 2002

(30) Foreign Application Priority Data

Oct. 20, 2000 (EP) .............................................. 00122915

(51) Int. Cl.$^7$ ............................ C12N 5/06; C12N 5/08; C12N 11/02; C12N 11/10; A61F 2/00
(52) U.S. Cl. ....................... 435/395; 424/423; 435/177; 435/178; 435/180
(58) Field of Search ................................. 435/174, 177, 435/178, 180, 395, 325; 424/423

(56) References Cited

U.S. PATENT DOCUMENTS

| 5,106,743 A | 4/1992 | Franzblau et al. | ........ 435/340.2 |
| 5,776,748 A | 7/1998 | Singhvi et al. | ............. 435/180 |
| 6,103,528 A | 8/2000 | An et al. | .................... 435/395 |

FOREIGN PATENT DOCUMENTS

EP      0 529 751      3/1993

OTHER PUBLICATIONS

Ho Tzyy–Chang et al: "Tissue culture of retinal pigment epithelium following isolation with a gelatin matrix technique." Experimental Eye Research, vol. 64, No. 2, 1997, pp. 133–139, XP001023547 ISSN: 0014–4835 *see Harvesting of cultured RPE on p. 134, left–hand column.
Benya P D et al: "Dedifferentiated Chordrocytes Reexpress the Differentiated Collagen Phenotype when Cultured in Agarose Gels" Cell, vol. 30, No. 1, 1982, pp. 215–224, XP001023689 ISSN: 0092–8674 *see Agarose culture on p. 222, left–hand column.
Hendrickson Dean A et al: "Phenotype and biological activity of neonatal equine chondrocytes cultured in a three–dimensional fibrin matrix," American Journal of Veterinary Research, vol 55, No. 3, 1994, pp. 410–414, XP001023610 ISSN: 0002–9645 *p. 411, left–hand column, last paragraph—right–hand column, paragraph 1; figures 1,2.

Kupper Jan–Heiner et al: "Improved protocols for the isolation and in–situ cryopreservation of cell colonies." Cytotechnology, vol. 21, No. 3, 1996, pp. 224–229, XP001023600 ISSN: 0920–9069 *p. 226, right hand–column, last paragraph 1—p. 227, right–hand column, last paragraph.
O'Connor Stephen et al: "Immobilization of neural cells in three–dimensional matrices for biosensor applications."Biosensors & Bioelectronics., vol. 14, No. 10–11, Jan. 2000, pp. 871–881, XP001023978 ISSN: 0956–5663 *see paragraphs 3.2.1 and 3.2.2.
Database WPI Section Ch, Week 200143 Derwent Publications Ltd., London, GB; AN 1994–220492 XP002176115 & JP 06 153928 A (Kubota Y), Jun. 3,1994.
Nagashima Masabumi et al: "Cortical Neurite Outgrowth and Growth Cone Behaviors Reveal Developmentally Regulated Cues in Spinal Cord Membranes." Journal of Neurobiology, vol. 39, No. 3, Jun. 5, 1999, pp. 393–406, XP000992295.
Tai Hsin–Chein et al: "Neurite Outgrowth and Growth Cone Morphology on Micropatterned Surfaces." Biotechnology Progress vol. 14, No. 3, May 1998, pp. 364–370, XP000992486.
Snow D M et al: "Sulfated Proteoglycans in Astroglial Barriers Inhibit Neurite Outgrowth in–vitro" Experimental Neurology, vol. 109, No. 1, 1990, pp. 111–130, XP000992420.
Hammarback J A et al: "Guidance of Neurite Outgrowth by Pathways of Substratum–Adsorbed Laminin" Journal of Neuroscience Research, vol. 13, No. 1–2, 1985, pp. 213–220, XP000997726.
Corey Joseph M et al: "Differentiated B104 Neuroblastoma Cells are a High–Resolution Assay for Micropatterned Substrates." Journal of Neuroscience Methods, vol. 75, No. 1, 1997 pp. 91–97, XP000992308.
Branch D W et al: "Microstamp Patterns of Biomolecules for High–Resolution Neuronal Networks" Medical and Biological Engineering and Computing, GB, Peter Peregrinus Ltd. Stevenage, vol. 36, No. 1, 1998, pp. 135–141, XP000727982.
Scholl M et al: "Ordered Networks of Rat Hippocampal Neurons Attached to Silicon Oxide Surfaces." Journal of Neuroscience Methods, vol. 104, 2000, pp. 65–75, XP000992294.

*Primary Examiner*—David M. Naff
(74) *Attorney, Agent, or Firm*—Frommer Lawrence & Haug LLP; William S. Frommer; Samuel H. Megerditchian

(57) ABSTRACT

The present invention relates to a method of forming a pattern of cells on a surface, the surface being prepatterned in having a pattern of cell-growth-promoting molecules and/or cell-growth inhibiting molecules attached thereon. The invention also relates to patterns of cells, artificial tissues and to a use thereof.

31 Claims, 5 Drawing Sheets

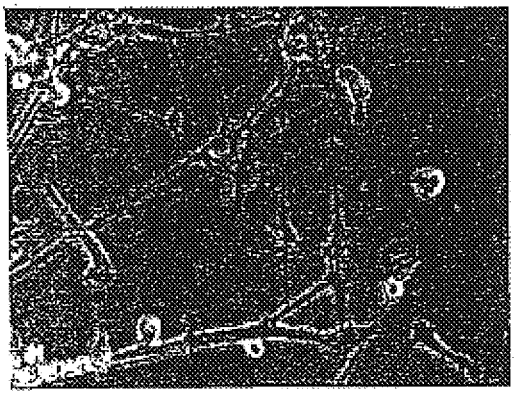
DA
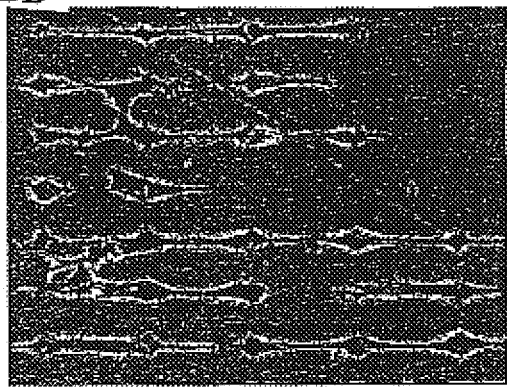
DB
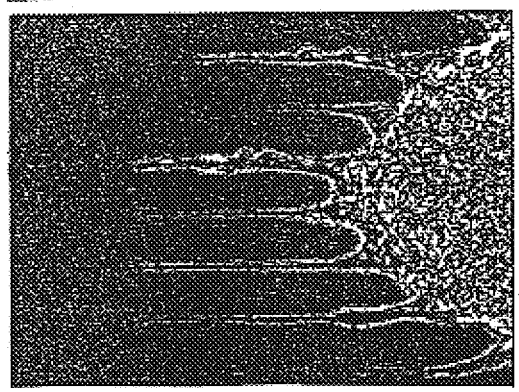
EA
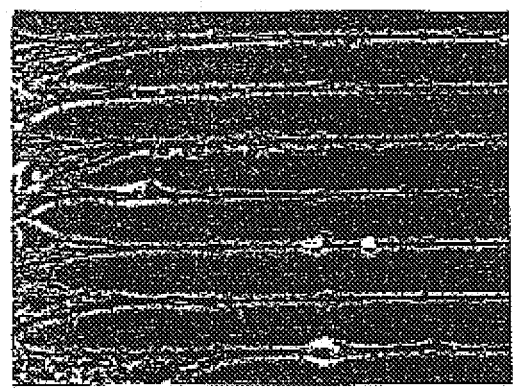
EB
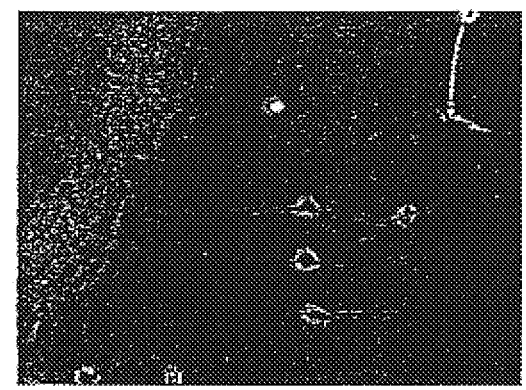
FA
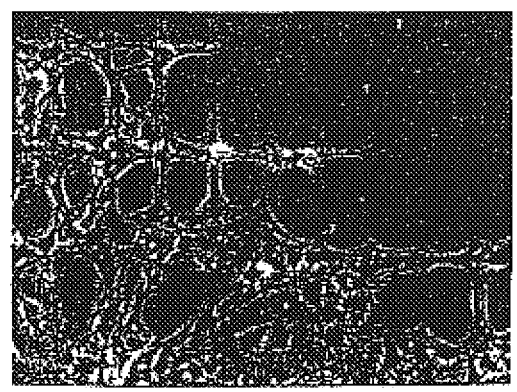
FB
Figure 3 (cont.d)

METHOD OF FORMING A CELL PATTERN ON A SURFACE

BACKGROUND OF THE INVENTION

In order to be able to study the functions of cells of various types so that their behaviour and spatial organisation in association with other cells of the same type can be better understood, it is necessary to be able to culture the cells under precisely controlled conditions. For a couple of years attempts have been undertaken to culture and grow cells on prepatterned substrates which guide the cell growth along the patterns on this substrate. This was done with the hindsight that, one day, one should be able to thereby build miniature biological electronic devices, incorporating live cells to make up a biological microcircuit. Another long-term goal of these studies is the capability of making artificial tissues suitable for implanting into an organism's body, thereby possibly replacing natural tissue of the same kind which is malfunctioning. A third aim of these studies is to be able to facilitate the integration of transplants and/or implants by "masking" the outer parts of these devices with a special array of cells which by their chemical and immunological nature as well as by their arrangement fit into the organism's body at the site in which the device is to be introduced.

One way of achieving cultures of cells to that extent, i.e. cultures which show a specific intended special pattern is to grow the cells along surfaces on which, previously, patterns of a "guiding" molecule which promotes cell growth have been created, and where there are regions which do not promote cell growth. Various cell growth promoting molecules have been used:

Mrksich et al. (1996, PNAS USA, 93, 10775–10778;1997, Exp. Cell Res., 235, 305–313) used alkanethiolate patterns on gold to control cell attachment to these substrates. By choosing an appropriately terminated alkanethiolate they succeeded in creating regions of cell growth promotion and cell growth inhibition. Corey et al. (1991, J. Neurosc. Res., 30, 300–307) managed to pattern neurons on polylysine-coated glass cover slips patterned by selective laser ablation so as to leave grids of polylysine with varying line widths, intrasection distances and nodal diameters.

Matsuzawa et al. (1996, J. Neurosci. Meth., 69, 189–196) chemically attached a synthetic peptide derived from a neurite-outgrowth-promoting domain of the B2 chain of laminin.

Others immobilised various other peptides (Matsuda et al., 1990, Trans. Am. Soc. Artif. Int. Organs; 36 (3): M559–63), or extracellular matrix proteins (ECM) such as laminin (Klein et al., 1999, J. Mat. Sci.: Mat. in Med.; 10: 721–727).

Various techniques for attaching and patterning biomolecules on a surface have been used, including crosslinkers (Clemence et al., 1985, Bioconjugated Chem. 6: 411–417), silane coupling agents (Plueddemann E. 2 edn New York Plenum Press, 1991: 1–250), amongst others. One recently and successfully applied technique to attach proteins in a specific pattern to a substrate is the so-called microcontact printing technique. It is comparatively simple and universal for patterning biomolecules (Kumar et al., 1993, Appl. Phys. Lett., 63 (14), 2002–2004). In this technique a stamp is produced by casting a silicon elastomer (polydimethyl siloxane, PDMS) in the desired pattern which is then coated with a solution of the biomolecule to be transferred. After contacting the "inked" stamp with the substrate surface the bio-molecules self-assemble in the pre-given pattern. Kumar et al. and Mrksich et al. developed this method of producing patterns by stamping alkane thiols on gold substrates (Mrksich et al. 1996, PNAS USA, 93, 10775–10778, Mrksich et al. 1997, Exp. Cell. Res. 235, 305–313). Poly-D-lysine and laminin have been immobilised using microcontact printing on amino silane derivatised glass substrates with glutaraldehyde as a cross linker (Branch et al. 1998, Med. Biol. Eng. Comput., 36, 135–141) and sulfo-GMBS (Wheeler et al. 1999, J. Biomech. Eng., 121, 73–78), and the technique of microcontact printing has been used in neuronal cell guidance (Wheeler et al. 1999, ibid.; Branch et al. 2000, IEEE Transact. Biomed. Eng., 47, 3, 290–300).

All of the aforementioned studies used dissociated cell cultures, mainly of neural origin and achieved successful pattern formation only in some cases. It is not clear, however, whether the patterns of cells thus formed do represent a true picture as it would appear in nature nor whether they are of any use, e.g. for bioelectronic devices. Therefore, the conclusions to be drawn from these studies, e.g. in respect of the spatial arrangement of cells within an organ or the interactions between cells within an organ are only of limited use. Likewise, if one looks at current bioelectronic interface devices and cell modified interfaces there is a problem of reproducibility in creating these devices. It is still not possible to fully control and guide cell attachment and growth on surfaces. Since with current bioelectronic interface devices and cell modified interfaces, the cells are being cultured directly onto the surface of these devices, there is no guarantee that growth on every device will be successful, and therefore a lot of devices and a lot of starter cultures are required just to ensure that some substrates, after culturing, may actually display a cellular network which is useful. A related problem concerning implants is that these are often only of limited biocompatibility due to their bad integration, a rejection by the host or simply the toxicity of the substrates. Lining them with a pattern of cells which mimic the spatial organisation of cells within an organ would certainly enhance the biocompatibility of implants.

OBJECTS AND SUMMARY OF THE INVENTION

Accordingly, one object of the present invention is to be able to control and guide cell growth on surfaces in a precise and hitherto unheard of manner. Another object of the present invention is to be able to limit the efforts in producing bioelectronic devices by reducing the number of starter cultures/substrates that will give a successful device. Another object of the present invention is to enhance that biocompatibility of implants and transplants.

The object is solved by
a method of forming a pattern of cells on a surface, said surface being prepatterned in having a pattern of cell-growth promoting molecules and/or cell-growth inhibiting molecules attached thereon, characterised in that cells are cultured on said prepatterned surface such that they form a pattern of cells on said surface, said cells being whole tissue.

Preferably said whole tissue is derived from an organism's body.

In one embodiment said whole tissue is derived from an organ selected from the group comprising brain, liver, kidney, muscle, skin, bone, lung and heart.

It is preferred that said cells are organ slices.

These organ slices are preferably organotypic in that they mimic the arrangement of cells within an organ.

Preferably said cells are brain slices.

In one embodiment said pattern of cell-growth promoting molecules and/or cell-growth inhibiting molecules attached on said prepatterned surface, allows for the guided growth and migration of cells, wherein preferably, said pattern of cell-growth promoting molecules and/or cell-growth inhibiting molecules mimics the arrangement of cells in an organ.

It is preferred that said pattern of cell-growth promoting molecules and/or cell-growth inhibiting molecules has a structure with lines and nodes, wherein preferably, said lines have a width in the range from 1–8 micrometers and said nodes have a diameter in the range from 1–30 micrometers, more preferably, said lines have a width in the range from 1–6 micrometers and said nodes have a diameter in the range from 8–16 micrometers, and most preferably, said lines have a width in the range from 2–4 micrometers and said nodes have a diameter in the range from 10–14 micrometers.

In one embodiment said pattern of cell-growth promoting molecules and/or cell-growth inhibiting molecules is formed by at least one layer of a substance selected from the group comprising polypeptide, polyethyleneimine and polystyrene wherein, preferably, said polypeptide is selected from the group comprising extracellular matrix proteins, poly-L-lysine and poly-ornithine, wherein, more preferably, said extracellular matrix proteins are selected from the group comprising laminin and fibronectin.

The object is also solved by a method of forming a pattern of cells on a surface, said surface being prepatterned in having a pattern of cell-growth promoting molecules and/or cell-growth inhibiting molecules attached thereon, in particular according to any of the preceding claims, characterised in that cells are cultured on said prepatterned surface such that they form a pattern of cells on said surface, said cells being selected from the group comprising whole tissue and dissociated cells, further characterised in that said pattern of cells, after having been formed on said prepatterned surface, is transferred to a second surface in a transfer step. wherein preferably, said transfer step comprises the sequence:

a) embedding said pattern of cells in a matrix,
b) lifting said matrix including said pattern of cells from said prepatterned surface,
c) contacting said pattern of cells embedded in said matrix with said second surface.

In one embodiment said transfer step further comprises the sequence:

d) releasing said pattern of cells from said matrix,
e) removing said matrix from said pattern of cells.

Preferably said matrix is a cell-compatible matrix.

A cell-compatible matrix is a matrix that does not interfere with the viability of cells used.

It is preferred that said matrix is a matrix composed of a material selected from the group comprising agarose, fibrin, collagen and cellulose.

In one embodiment said matrix is a matrix composed of a curable material, wherein preferably, said curable material is selected from the group comprising agarose.

In one embodiment said matrix is a matrix composed of a material capable of forming a gel, wherein, preferably, said material capable of forming a gel is selected from the group comprising fibrinogen and collagen.

In one embodiment said second surface is selected from the group comprising surfaces of bioelectronical devices, sensors, electronic components, tissues, implants and transplants.

"Sensors" are meant to include biosensors, optical sensors, amongst others. "Electronic components" can, for example, be field-effect transistors, multi-electrode arrays and the like. Transplants can be of any form known, i.e. autogenous (donor and receptor identical), syngenous (genetically identical donor and receptor), allogenous (donor and receptor belong to the same species) and xenogenous (donor and receptor belong to different species).

In one embodiment said embedding is achieved aa) partially or fully covering said pattern of cells with said matrix in a liquid form, and
ab) forming said matrix.

It is preferred that forming said matrix (ab)) is achieved by increasing the temperature above the gel-transition temperature and/or addition of at least one gel-inducing component, wherein, preferably, said gel-inducing component is selected from the group comprising thrombin and other blood-coagulation factors.

It is preferred that said releasing said pattern from said matrix is achieved by enzymatic degradation and/or lowering the temperature below the gel-transition temperature.

The object of the present invention is also solved by a pattern of cells and/or an artificial tissue sue producable by a method according to the present invention up to, but exclusive of the transfer step.

The object is furthermore solved by a pattern of cells and/or an artificial tissue on a surface producable by a method according to the present invention up to, but exclusive of the transfer step.

It is also solved by a pattern of cells and/or an artificial tissue producable by the method according to the present invention including the transfer step and various embodiments thereof.

The object is also solved by a pattern of cells and/or an artificial tissue on a surface producable by the method according to the present invention including the transfer step and various embodiments thereof.

The object of the present invention is also solved by a combination of patterns of cells according to the present invention.

The object is furthermore solved by a combination of artificial tissues according to the present invention.

It is also solved by a combination of patterns of cells and artificial tissues according to the present invention.

The term "combination of patterns of cells" is meant to include any spatial arrangement of patterns of cells wherein these patterns are in proximity to each other. The same applies to "combination of artificial tissues".

The object is furthermore solved by the use of a pattern of cells and/or an artificial tissue and/or a combination according to the present invention in a device selected from the group comprising sensors, technical substrates, tissues, implants and transplants.

BRIEF DESCRIPTION OF THE DRAWINGS

Further advantages and aspects of the present invention can be taken from the following examples and figures, although the invention is by no means limited thereto. In the figures.

DETAILED DESCRIPTION OF THE INVENTION

Figure 1:
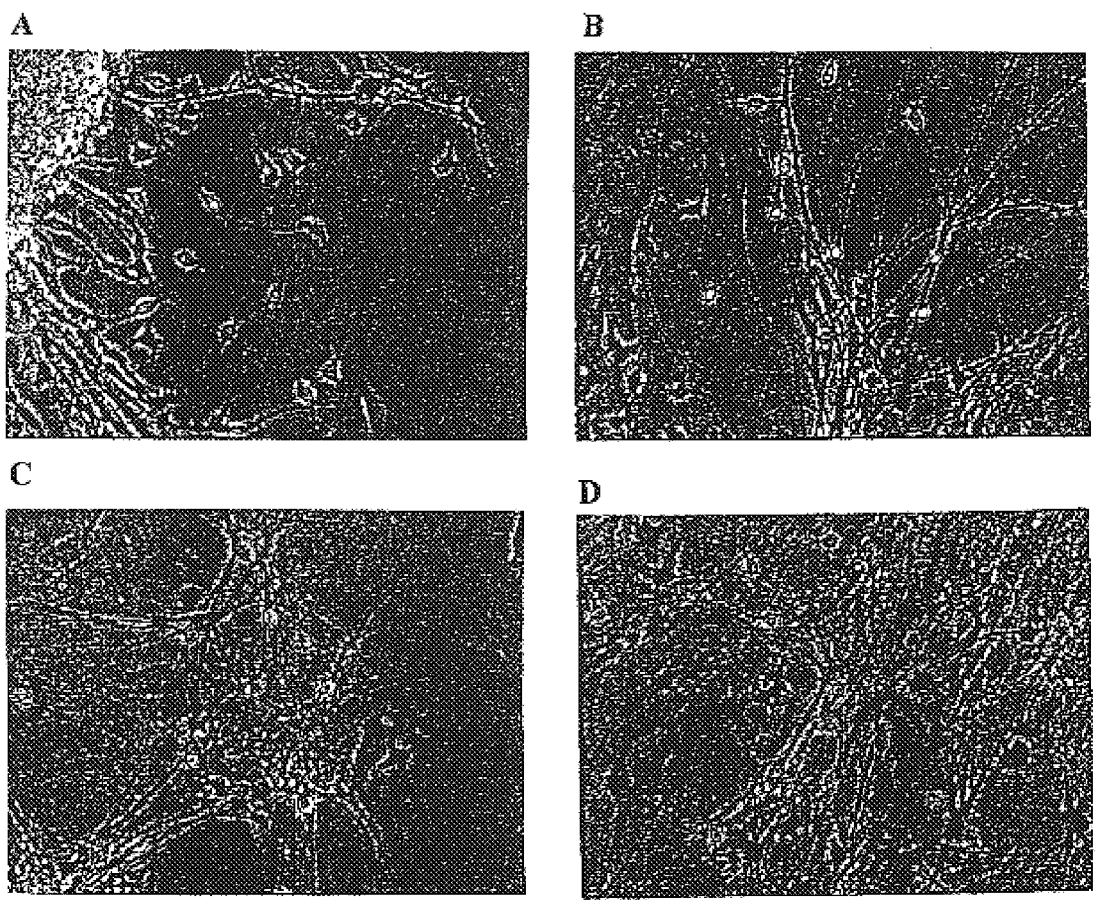
FIG. 1 shows the migration of organtypic brain stem neurons on laminin-coated tissue culture plastic.

The inventors, in making the present invention, could clearly demonstrate that it is possible to manipulate cells of organ slices onto a number of best suited patterns. In using cells from whole tissue, extended, almost perfect patterns of cells, e.g. grids, could be achieved which were hitherto impossible. The use of whole tissue slices has many advantages over dissociated cultures in that, apart from the superficial layer, relatively minimal mechanical damage is being inflicted and the relative cytoarchitectural organisation of the tissue is preserved. The subsequently patterned cells will thus, reflect the relative positions of cells of the original slice. By means of the present invention it is possible to consistently achieve, e.g., outgrowth of neurons, neurites and filopodia from brain stem slices cultured on ECM protein structures of, e.g. grid- and line-shapes. By choosing appropriate patterns of cell-growth promoting molecules and/or cell-growth inhibiting molecules on a surface it is possible to achieve almost any pattern of cells desired.

Furthermore, the present inventors managed to further manipulate the almost perfect patterns of cells in that they could easily transfer these patterns onto any other surface desired. Such a transfer can, for example, be performed by embedding the pattern/artificial tissue in materials, which are compatible with the cells in that they do not interfere with the cells' viability. Such a material can for example be agarose which is poured in liquid form over the pattern of cells and thereafter cured by allowing it to cool. An alternative method would be the embedding of cells in a gel of fibrin and/or collagen. For example, fibrinogen can be induced to form a gel of fibrin by the addition of thrombin. Modifications of this method, wherein prothrombin is added in combination with various factors from the blood-clotting cascade, e.g. factor X, are also within the scope of the present invention. Methods of forming fibrin-gels are, for example, described in Schense et al., 2000, Nature Biotechnology, 18, 415–419 and Ye et al., 2000, European Journal of Cardio-thoracic Surgery, 17, 587–591 and are included herein by reference.

Collagen-gels can be formed by self-assembly of collagen molecules upon warming cold neutral solutions of collagen. Such a method is, for example, described in O'Connor et al., 2000, Biosensors and Bioelectronics, 14, 871–881, and is explictly included herein by reference.

According to the present invention all matrices, independent of their nature, are assembled on a pattern of cells/artificial tissue that has already been formed on a surface. This means, that according to the present invention the matrix is formed only after the formation of the pattern of cells/artificial tissue. By means of the gel, the pattern of cells can then be tranferred elsewhere.

Removal of the matrix can then, for example, be achieved by lowering the temperature below the gel-transition temperature, enzymatic degradation and the like.

This makes the production of bioelectronic devices much more economical and allows for precise control of the characteristics of these devices since only successful patterns of cells will be used and transferred onto the surfaces of these devices. Once a perfect pattern of cells is formed, it can be stabilised using a matrix and removed from the substrate and transferred onto biosensors, such as field effect transistors etc. which in themselves might not be suited as substrates for cell-growth in the first place. With a "pre-cultured-situation" according to the present invention, only useful patterns of cells will be used and transferred onto the devices. Thus the number of devices that are required can be better controlled. This is true for all the other applications mentioned and gives a huge flexibility to possible applications. This "off-the-shelf-approach" is very useful when the device availability is limited, the device itself is not so well suited for cell-growth and culture, or when the further manipulation of cells on these devices causes irreversible damage to the cells. In this case a new pattern of cells (grown on a prepatterned substrate) can be placed onto the same device and the measurements (of whatever kind that is to take place with this particular device) can be resumed. Alternatively, the pattern of cells used in one device can be transferred into sterile conditions (i.e. taken off the device) and then be returned to the incubator for a further period of culture.

The present inventors, using a combination of organotypic whole tissue and carefully designed prepatterned surfaces, managed to produce a huge variety of patterns of cells. According to any requirement (depending on the device) further patterns can be designed. Although the microcontact printing technique is discussed herebelow as a suitable technique for creating a surface which is prepatterned in having cell-growth promoting molecules and/or cell-growth inhibiting molecules attached thereon, the present invention is by no means intended to be restricted to this particular technique. Other techniques for creating prepatterned surfaces like photolithography, laser ablation techniques with lithographic masks etc. are envisaged, too.

EXAMPLE 1

Using the present invention a huge variety of patterns of laminin on a surface could be successfully employed in the present invention. These patterns, in which a precise control of the cell-growth could be achieved, are shown in table 1

TABLE 1

| pattern | structure | dimensions | scheme |
|---------|-----------|------------|--------|
| 1 | lines | lines: 2 μm<br>distance: 100 μm |  |
| 2 | lines | lines: 4 μm<br>distance: 100 μm |  |
| 3 | lines | lines: 6 μm<br>distance: 100 μm |  |

TABLE 1-continued

| pattern | structure | dimensions | scheme |
|---|---|---|---|
| 7 | grid with nodes | lines: 2 μm<br>nodes: 10 μm<br>mesh: 100 × 50 μm |  |
| 8 | grid with nodees | lines: 4 μm<br>nodes: 12 μm<br>mesh: 100 × 50 μm | 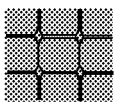 |
| 9 | grid with nodes | lines: 6 μm<br>nodes: 14 μm<br>mesh: 100 × 50 μm | 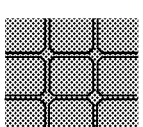 |
| 10 | lines with nodes | lines: 2 μm<br>nodes: 20 μm<br>line distance: 50 μm<br>node distance: 100 μm | 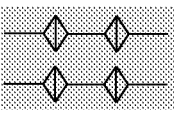 |
| 11 | lines with nodes | lines: 4 μm<br>nodes: 22 μm<br>line distance: 50 μm<br>node distance: 100 μm | 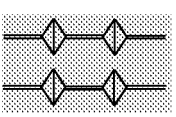 |
| 12 | lines with nodes | lines: 2 μm<br>nodes: 10 μm<br>line distance: 50 μm<br>node distance: 100 μm | 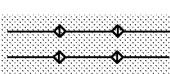 |
| 13 | grid with nodes | lines: 2 μm<br>nodes: 20 μm<br>mesh: 100 × 50 μm | 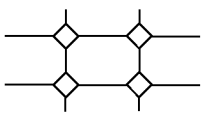 |
| 14 | grid with nodes | lines: 4 μm<br>nodes: 22 μm<br>mesh: 100 × 50 μm | 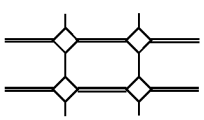 |
| 15 | grid with nodes | lines: 6 μm<br>nodes: 24 μm<br>mesh: 100 × 50 μm | 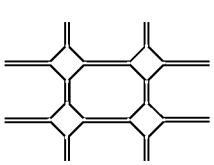 |
| 24 | grid with nodes and gaps | lines: 4 μm<br>nodes: 22 μm<br>gaps: 20 μm<br>mesh: 100 × 50 μm | 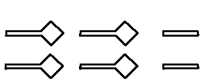 |
| 30 | cascade (increasing) with dotted lines | lines: 2 μm<br>nodes: 20 μm<br>dots: 5 μm<br>line distance: 50 μm<br>node distance: 100 μm | 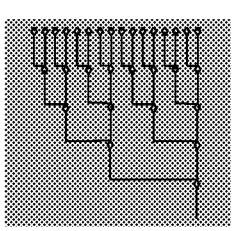 |

TABLE 1-continued

| pattern | structure | dimensions | scheme |
|---|---|---|---|
| 34 | series connection | lines: 2 μm<br>nodes: 20 μm<br>line distance: 100 μm<br>node distance: 100 μm | |

EXAMPLE 2

Organotypic Cultures of Brain Stem Slices

Upon extraction of the whole embryonic 15–18 days old Sprague-Dawley rat brains, the medulla and pons were removed by a transverse section through the rostral pons and the cerebellum removed by sectioning the peduncles. Coronal sections of brain stem slices were harvested in sterile conditions in chilled brain slice culture medium (pH 7.4). These slices, which were cut using McIlwain Tissue Chopper, were 250 μm thick. The thus prepared slices (usually about 6 to 12 slices per rat brain stem) were placed in an incubator at 37° C. and a 5% $CO_2$ enriched atmosphere for 4–5 hours minimum. This incubation period was provided in order to allow damaged cells (as a result of slicing) to detach from the surfaces of the cut slices. After this incubation period, the slices were then positioned onto controls (laminin-coated) and test substrates (laminin-patterned) using a small surface-polished spatula. Care has to be taken not to further damage the prepared slices. Unlike the method described by Gähwiler (1997, Trends in Neurosci., 20 (10), 471–477) plasma clot or collagen was not used in immobilising the slices as either method would hinder cell migrations, particularly migrations onto ECM patterns. Furthermore, the roller tube technique was deemed unnecessary. Instead, in all culture dishes, a critical amount of medium was added such that the slices did not detach from the surface. After 2–3 days in culture, the slices should have undergone significant extent of migration and more medium could be added at that stage. Antimitotic agent, cytosine β-D-arabinofuranoside (ARA-C, SIGMA C-6645), was added on day 4 or 5 to inhibit non-neuronal cells proliferation if and when necessary. If ARA-C was used, the culture medium was reverted back to ARA-C-free after 5 to 7 days.

EXAMPLE 3

Micro Contact Printing and Solutions

Microstamps for the experiment were produced by photolithography and moulding. An electron beam writer transposed the different structures designed for the experiment to a chrome mask. Applying UV-photolithography, master moulds were produced out of spin coated 12.5 μm thick photoresist layers (AZ 4562, Clariant GmbH, Germany) on 0.6 mm thick silicon wafers (MEMC Electronic Materials, Germany). Polydimethylsiloxane (PDMS) microstamps were then fabricated curing Sylgard 182 (Dow Corning, Germany) in 10 ml eppendorf tubes for 48 hours at 55° C. upside down on the master moulds. After master mould release final curing was performed for 1 h at 110° C. In order to increase the stamp hydrophilicity, PDMS stamps were stored in deionized water for a minumum of 24 hours. Prior to patterning, stamps were taken out of the water and sterilised in a 70% ethanol bath for 1 minute. Inking took place for 30 seconds in 25 μg/ml (~0.25 μM) of laminin solution. The inked stamp was then dried in a soft nitrogen airstream and immediately pressed onto the substrate for 10 seconds. In all experiments, non tissue culture polystyrene petri dishes of 3 cm diameter (Greiner Labortechnik, Germany) were used.

Brain slice medium was made from HAMS F10 (SIGMA; N1387) supplemented with 20–25% foetal bovine serum (SIGMA, F7524) and 4 mM glutamine (SIGMA, G7513). Laminin (1243217, Boehringer Mannheim GmbH, Germany) was re-constituted in sterile PBS.

EXAMPLE 4

Patterns of Cells Achived

FIG. 1 shows the migration of organotypic brain stem neurons on laminin-coated tissue culture plastic. On day 3 (FIG. 1A) in culture, migrated neurons were clearly identifiable and growth of neurites had already begun. On day 5 (FIG. 1B), these dendritic and axonal processess had grown to significant length. By 13 (FIG. 1C) and 20 days (FIG. 1D), the culture became confluent with all the neurons forming a diffused network on top of glial cells and other non-neuronal cells.

Figure 2:
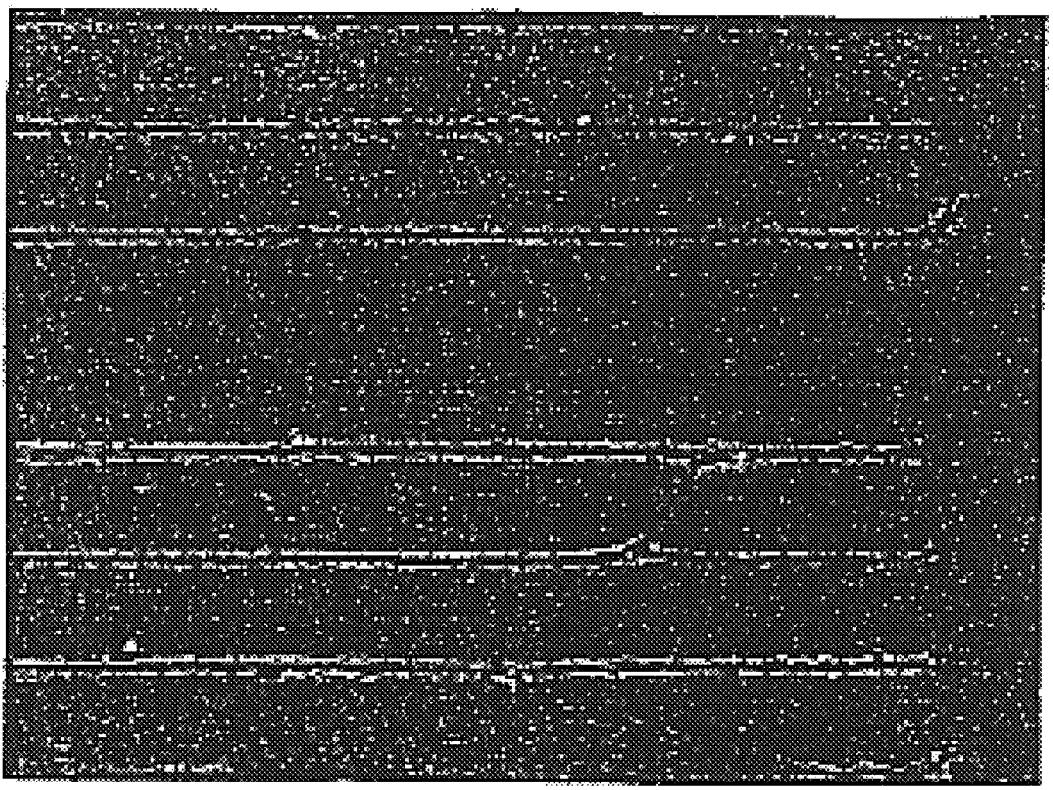
FIG. 2 shows the growth of neuritis on laminin tracks.

FIG. 2 shows the effectiveness by which neurite outgrowth and neuronal migration can be guided by using the technique of the present invention. Regardless of the pattern used, brain stem slices on laminin patterned substrates displayed a rapid growth of neurites, and these extended to the edge of the stamped patterns within two weeks. By the end of two weeks, the axons reached maturity and became thickened.

Figure 3:
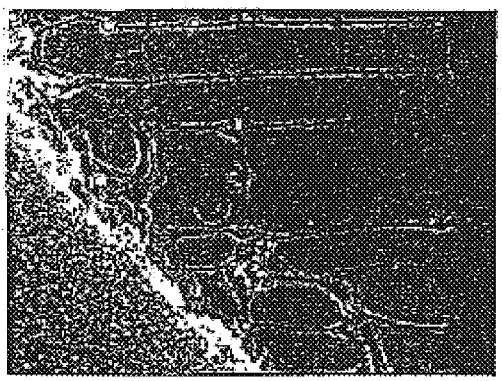
FIG. 3 shows the evaluation of a variety of extracellular matrix protein patterns.
Figure 3:
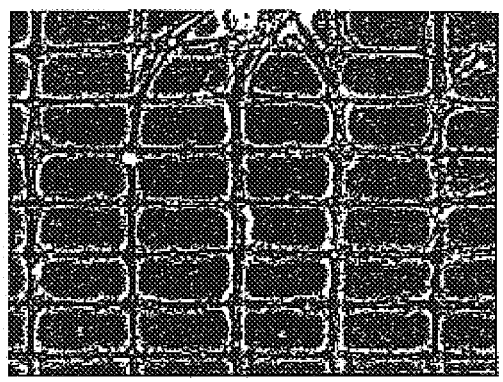
Figure 3:
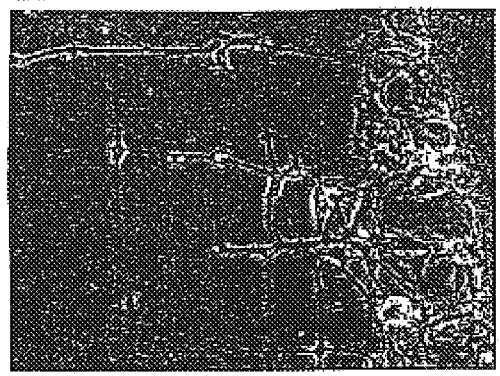
Figure 3:
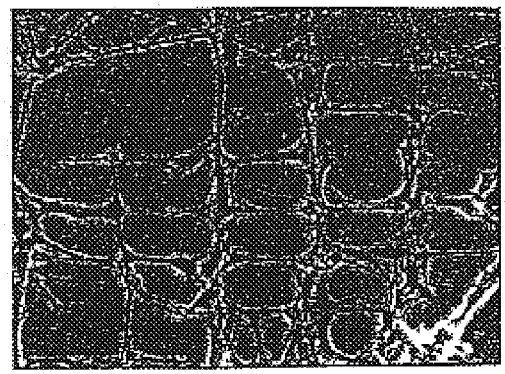
Figure 3:
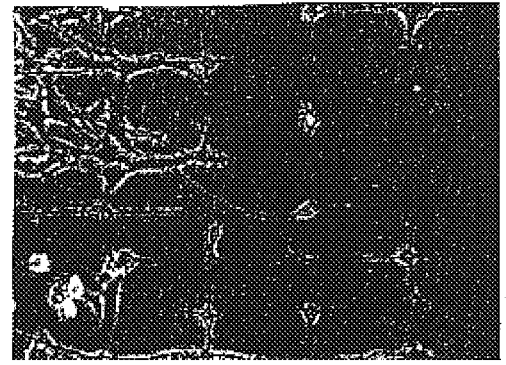
Figure 3:
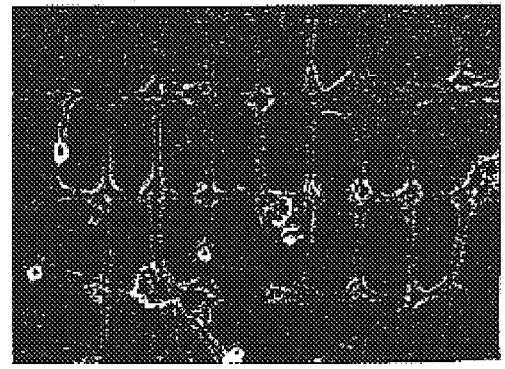

FIG. 3 shows the evaluation of a variety of extracellular matrix proteins patterns. (FIGS. 3AA and 3AB) Pattern 1, node 10 μm, track 2 μm; (FIGS. 3BA and 3BB) Pattern 2, node 10 μm, track 4 μm); (FIGS. 3CA and 3CB) Pattern 3, node 10 μm, track 6 μm; (FIGS. 3DA and 3DB) Pattern 4, node 10 μm, track 2 μm; (FIGS. 3EA and 3EB) Pattern 5, node 10 μm, track 2 μm; (FIGS. 3FA and 3FB) Pattern 6, node 20 μm, track 4 μm. During early days in culture, the migrated neurons and growing processes were clearly visible with little overlapping on all the patterns. These cultures continued to mature and by 10 days or more, the original shapes of the laminin stamped patterns were identifiable.

Figure 4:
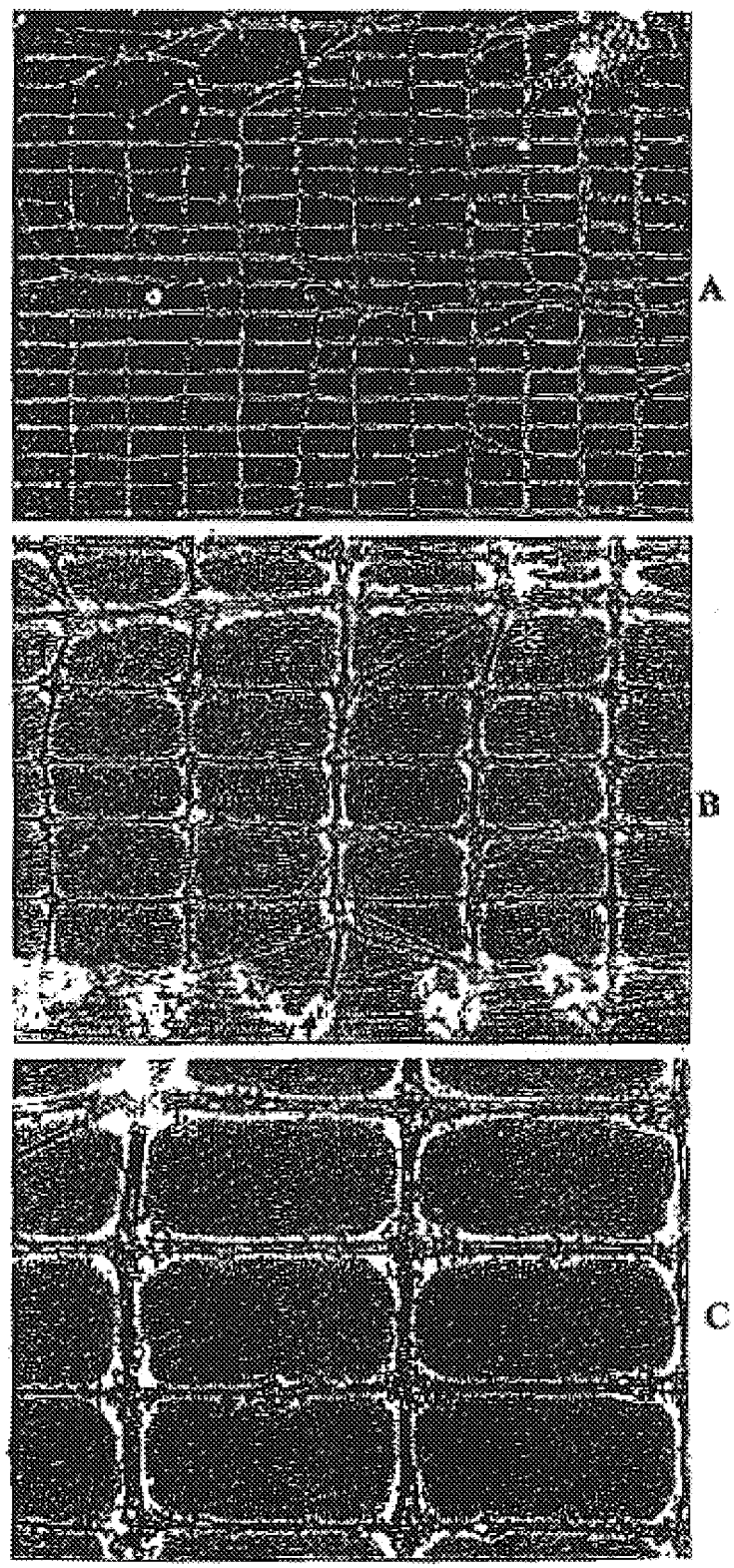
FIG. 4 shows the growth of neuronal processes.

FIG. 4 shows that nearly perfect patterns could be achieved using a 2 μm line width (node diameter=10 μm) and a perfect grid structure could be formed. The figure shows the growth of neuronal processes on Pattern 1, 14 days old culture at progressively increasing magnification of ×40 (FIG. 4A), ×100 (FIG. 4B), ×200 (FIG. 4C). This perfect network of processes was obtained with pattern of the smallest track (2 μm). * indicate the same point of the substrate at their corresponding magnifications. With this particular pattern, however, very few visually identifiable neurons actually migrated to the pattern, which, in turn, is exclusively formed from neurite outgrowth. Patterns with node size of 10–14 μm and line width of 2–4 μm were the most appropriate for the confinement of neurons. Experiments using various line widths showed the best neuronal migration occurred with a 6 μm line width, where a perfect network of processes had occupied approximately the same area of the original stamp (10 mm diameter) used for the microcontact printing technique. It is known that cells tend to migrate towards the nodes (Klein et al., 1999, J. of Mat. Sci: Mat. in Med., 10, 721–729; Corey et al., 1991, J. of Neurosci. Res., 30, 300–307) and the same phenomenon was observed with brain sliced neurons. These neurons became immobilised once migrated onto the nodes. After a number of days in culture, the neuronal processes of the neurons were beginning to grow and were forming a simple linear neuronal network.

The features of the present invention disclosed in the specification, the claims and/or in the accompaning drawings, may, both seperatly, and in any combination thereof, be material for realizing the invention, in various forms thereof.

What is claimed is:

1. A method of forming a pattern of cells on a surface, comprising the step of culturing said cells on a prepatterned surface to form a pattern thereon, wherein said prepatterned surface comprises a pattern of cell-growth promoting molecules or cell-growth inhibiting molecules attached thereon, wherein said cells are from whole tissue, wherein said whole tissue is placed on said pattern of cell growth promoting molecules or cell-growth inhibiting molecules, and wherein said pattern of cell-growth promoting molecules or cell-growth inhibiting molecules allows for the guided growth and migration of cells.

2. The method according to claim 1, wherein said whole tissue is derived from an organism's body.

3. The method according to claim 1, wherein said whole tissue is derived from an organ selected from the group consisting of brain, liver, kidney, muscle, skin, bone, lung and heart.

4. The method according to claim 1, wherein said cells are from organ slices.

5. The method according to claim 4, wherein said cells are from brain slices.

6. The method according to claim 1, wherein said pattern of cell-growth promoting molecules or cell-growth inhibiting molecules mimics the arrangement of cells in an organ.

7. The method according to claim 1, wherein said pattern of cell-growth promoting molecules or cell-growth inhibiting molecules has a structure with lines and nodes.

8. The method according to claim 7, wherein said lines have a width in the range from 1–8 micrometers and said nodes have a diameter in the range from 1–30 micrometers.

9. The method according to claim 8, wherein said lines have a width in the range from 1–6 micrometers and said nodes have a diameter in the range from 8–16 micrometers.

10. The method according to claim 9, wherein said lines have a width in the range from 2–4 micrometers and said nodes have a diameter in the range from 10–14 micrometers.

11. The method according to claim 1, wherein said pattern of cell-growth promoting molecules or cell-growth inhibiting molecules is formed by at least one layer of a substance selected from the group consisting of polypeptide, polyethyleneimine and polystyrene.

12. The method according to claim 11, wherein said polypeptide is selected from the group consisting of extracellular matrix proteins, poly-L-lysine and poly-ornithine.

13. The method according to claim 12, wherein said extracellular matrix proteins are selected from the group consisting of laminin and fibronectin.

14. The method according to claim 1, further comprising the step of transferring said pattern of cells to a second surface after said pattern of cells are formed on said patterned surface.

15. The method according to claim 14, wherein said transfer step comprises the steps of:
embedding said pattern of cells in a matrix;
lifting said matrix including said pattern of cells from said prepatterned surface; and
contacting said pattern of cells embedded in said matrix with said second surface.

16. The method according claim 15, wherein said transfer step further comprises the steps of:
releasing said pattern of cells from said matrix; and
removing said matrix from said pattern of cells.

17. The method according to claim 15, wherein said matrix is a cell-compatible matrix.

18. The method according to claim 15, wherein said matrix is a material selected from the group consisting of agarose, fibrin, collagen and cellulose.

19. The method according to claim 15, wherein said matrix is a matrix comprised of a curable material.

20. The method according to claim 19, wherein said curable material comprises agarose.

21. The method according to claim 15, wherein said matrix is a matrix comprised of a material capable of forming a gel.

22. The method according to claim 21, wherein said material capable of forming a gel is selected from the group consisting of fibrinogen and collagen.

23. The method according to claim 14, wherein said second surface is selected from the group consisting of surfaces of bioelectrical devices, sensors, electrical components, tissues, implants and transplants.

24. The method according to claim 15, wherein said embedding step comprises partially or fully covering said pattern of cells with said matrix in a liquid form; and forming said matrix.

25. The method according to claim 24, wherein said forming step comprises increasing the temperature above the gel-transition temperature and/or addition of at least one gel-inducing component.

26. The method according to claim 25, wherein said gel-inducing component is selected from blood-coagulation factors.

27. The method according to claim 16, wherein said releasing step comprises enzymatic degradation and/or lowering the temperature below the gel-transition temperature.

28. A pattern of cells on a surface produced by a method according to claim 1.

29. A pattern of cells on a surface produced by a method according to claim 14.

30. A combination of a plurality of patterns of cells produced by the method according to claim 1.

31. The method according to claim 26, wherein said blood coagulation factor is thrombin.

* * * * *